(12) United States Patent
Yamamoto

(10) Patent No.: US 6,585,638 B1
(45) Date of Patent: Jul. 1, 2003

(54) ENDOSCOPE POWER SUPPLYING APPLIANCE

(76) Inventor: Hidehiro Yamamoto, 11-5, Akashia-dai 5-chome, Mita-shi, Hyogo 669-1323 (JP)

(*) Notice: Subject to any disclaimer, the term of this patent is extended or adjusted under 35 U.S.C. 154(b) by 0 days.

(21) Appl. No.: 09/787,223

(22) PCT Filed: Sep. 17, 1999

(86) PCT No.: PCT/JP99/05054

§ 371 (c)(1),
(2), (4) Date: Mar. 16, 2001

(87) PCT Pub. No.: WO00/16707

PCT Pub. Date: Mar. 30, 2000

(30) Foreign Application Priority Data

Sep. 18, 1998 (JP) .......................................... 10-303145

(51) Int. Cl.[7] ............................................... A61B 17/39
(52) U.S. Cl. ......................................... 600/114; 606/41
(58) Field of Search ............................... 606/46–47, 41; 600/114, 138, 101

(56) References Cited

U.S. PATENT DOCUMENTS

| | | | | |
|---|---|---|---|---|
| 5,007,907 A | * | 4/1991 | Nishigaki et al. | 606/46 |
| 5,088,998 A | * | 2/1992 | Sakashita et al. | 606/46 |
| 5,472,441 A | * | 12/1995 | Edwards et al. | 606/41 |
| 5,718,702 A | * | 2/1998 | Edwards | 606/41 |
| 5,938,661 A | * | 8/1999 | Hahnen | 606/46 |

FOREIGN PATENT DOCUMENTS

| | | |
|---|---|---|
| JP | 58-97415 | 1/1985 |
| JP | 59-36255 | 10/1985 |
| JP | 62-227348 A | 6/1987 |
| JP | 4-158870 A | 6/1992 |
| JP | 5-184535 A | 7/1993 |
| JP | 9-38103 A | 2/1997 |
| JP | 9-94214 A | 4/1997 |
| JP | 9-262244 A | 10/1997 |

* cited by examiner

*Primary Examiner*—John A. Jeffery
(74) *Attorney, Agent, or Firm*—Simpson & Simpson, PLLC

(57) ABSTRACT

An endoscope power supplying appliance comprising an operation unit, a cylinder unit and an electrode that is used by inserting an endoscope, wherein the electrode is set at the distal end of the cylinder unit and the operation unit at the other end, an optical lens portion of the endoscope inserted into the power supplying appliance is capable of protruding beyond the end of the power supplying appliance, and the endoscope can move along an axial direction of the power supplying appliance. Further the endoscope power supplying appliance of this invention is effective for treatment such as coagulation of microvessels performed under endoscope and in particular blocking operation of sympathetic nerves in the chest region performed under endoscope, only one minimized skin incision allows the operation. Because it is not necessary to insert the appliance or pull it out of the body during the operation, frictional irritation to the incised portion is only caused at the time of insertion and extraction of the appliance before and after the operation, which minimizes the damage of the incised portion. Consequently the patient does not necessarily hospitalize for a long time and may leave hospital and go home on the day of operation.

38 Claims, 4 Drawing Sheets

ENDOSCOPE POWER SUPPLYING APPLIANCE

FIELD OF THE INVENTION

This invention relates to an endoscope power supplying appliance, and in particular to an endoscope power supplying appliance capable of endoscopic surgical operation with a single skin incision. Further this invention relates to a power supplying appliance suitable for blocking operation of nerve fibers such as sympathetic nerves and parasympathetic nerves, and in particular, blocking operation of sympathetic nerves in thoracic part under thoracoscope.

BACKGROUND TECHNOLOGY

In conventional so called endoscopic operations, surgical operations using endoscope, an endoscope and operational devices such as electric knives and electrodes for cautery are inserted from different skin incisions. Consequently at least two skin incisions and in some cases more than three incisions are necessary in such operations. And bar shaped devices with no cavities are used for the operation devices such as electric knives and electrodes for cautery for perfect sterilization and prevention of pollution. Consequently cylindrical shaped devices are not used.

However to reduce patients' load and to facilitate earlier recovery after surgical operations, it is preferred to reduce the number of skin incisions and the size thereof. It is necessary to insert an endoscope and power supplying appliance from a same incision to finish off the operation with only one cut. Further it is necessary to make endoscope and power supplying appliance as thin as possible so as to minimize the size of incision. Conventionally there was no endoscope power supplying appliance that satisfies above requirements.

DISCLOSURE OF THE INVENTION

The present invention relates to an endoscope power supplying appliance of which an endoscope and an operational device can be inserted into a body from a same skin incision and procedures such as electric cautery, electrocoagulation and electro scission can be performed while observing an operation site through the endoscope to resolve above said problems. More specifically, this invention relates to an endoscope power supplying appliance in a cylindrical shape having an electrode for electric coagulation and electro scission at a distal end of the cylinder in which an endoscope can be inserted and moved minutely along the cylinder. Further the present invention relates to an endoscope power supplying appliance having a slit at the distal end of the appliance.

The power supplying appliance of this invention used while an endoscope is inserted therein is composed of a control unit, a cylinder unit and an electrode, where the electrode is set at the distal end of the cylinder unit, the control unit at the other end of the cylinder unit, the optical lens of the endoscope inserted in the power supplying appliance can protrude beyond the distal end of the power supplying appliance and the endoscope can move in the axial direction of the power supplying appliance. The endoscope is composed of a bar-shaped insert part in diameter of 2 mm to 3 mm having an optical lens at the distal end thereof and a display unit attached thereto such as TV monitor. Commercial endoscopes for surgery operation under endoscope may be optionally used for the endoscope of the present invention. The insert part having an optical lens inserted into the power supplying appliance of this invention must be inserted while nearly contacting inside wall of the hard power supplying appliance, and should be a linear shape or a curved shape with a constant radius having a constant sectional shape so that the insert part can move minutely in the axial direction of the cylinder unit. Although the sectional shape of the insert part is optional, a round shape conforming to the optical system of the endoscope is generally preferred.

The power supplying appliance is formed of a hard and tough material such as metals, for example, stainless steal and ceramics. The appliance has an electrode at the distal end of the cylinder unit where the electrode is electrically connected to the control unit. When the cylinder unit of the appliance is made of an electroconductive material such as metal, the outside wall and inside wall of the cylinder unit except for the electrode must be insulated from the outside in order not to connect to the endoscope. The insulation treatment may be performed by coating treatment, coating and hardening, baking finish of an insulation material. Although the electrode may be monopolar or bipolar, monopolar is preferred when performing a micro-structural operation because the monopolar electrode is capable of concentrating electric power in a comparatively narrow area.

When the distal end of the power supplying appliance is used for incision, it is preferred to make the distal end sharp as a blade. Further it is preferred to arrange the optical lens of the endoscope close to the distal end of the cylinder unit so as not to form a too broad gap between the lens and the distal end. In case too broad gap is formed between the optical lens and the distal end, body liquid such as blood, fat, body tissue fragments formed during the incision will intrude the gap during the operation, which will contaminate other parts in the body or raise troubles to the endoscopic observation by narrowing the view through the endoscope.

The optical lens of the endoscope of the endoscope power supplying appliance of this invention can protrude beyond the distal end of the cylinder unit, and the endoscope may be moved minutely in the axial direction of the cylinder unit to a specific position. Endoscopic observation is facilitated by protruding beyond the distal end of the cylinder unit because the endoscopic view is not disturbed by the cylinder unit. Further since the lens is capable of moving a specific position in the axial direction of the cylinder unit, an operator can observe an operation site in the body with a wide view to specify the target area of the operation by protruding the endoscope beyond the distal end of the cylinder unit when looking for an operation site, and when performing the operation, it is possible to focus both on the subject area and on the electrode concurrently by pulling it in the cylinder unit. The distance of the movement is very short and generally 5 mm to 7 mm is sufficient. By adopting above said configurations, it is possible for the operator to keep the electrode always in his/her view when performing the treatment with the electrode because the electrode and the endoscope move along the same axial line, and further the operator is capable of performing a cautery while precisely approaching the electrode to the operation site specified by the search. The movement of the endoscope may be done manually or electrically by linear motor and the like. In the case of electric-motor driven devices, the linear motor may be controlled by dials, levers and the like on the control unit, which is capable of moving the lens to a desired position through one-touch operation and facilitates the control during operation. It is not necessary to take the endoscope out of the body each time during operation.

Further it eliminates the need for procedures such as checking on the direction of the view and focusing each time the endoscope or electrode is moved, the operation is facilitated and may be proceeded promptly because the moving direction of the endoscope and the power supplying appliance and viewing direction of the endoscope become all concentric.

The electrode at the distal end of the cylinder unit must have a shape which does not block the movement of the endoscope so that the endoscope can protrude beyond the distal end of the cylinder unit in order that the electrode or the distal end of the cylinder unit may not get in the view of endoscope. Consequently when the insert part of the endoscope has a circular section, it is preferred that the electrode also has a circular shape or an arc shape constituting a part of the circular shape conforming to the sectional shape of the endoscope. When adopting bipolar electrode, in particular, it is preferred to configure an arc shape. The electrode may be cylinder shape of which distal end cutting perpendicular to an axial direction or cutting on the slant to the axial direction, or further the distal end can be a needle shape or a linear shape. The electrode in the needle shape or the linear shape enable operations such as micro-area cautery or coagulation and electric stimulation for searching by the electrode. For example, when an operator want to identify a nerve fiber to block among a bundle of nerve fibers, week electric stimulations may be conducted to respective nerve fibers by the distal end of the needle shape electrode and observing the response against the stimulation, the operator can confirm which part of the body the nerve fiber connects to. Further blocking of a specific nerve fiber is made possible by the needle shape electrode in the nerve blocking operation which is conventionally very difficult to do.

Further the endoscope power supplying appliance of this invention is effective to treatments such as coagulation of microvessels performed under endoscope and only one minimized skin incision allows the operation, in particular, in the, case of blocking operation of sympathetic nerves in the chest region performed under endoscope. Because it is not necessary to insert the device into the body or pull it out of the body each time changing the device during the operation, the case of frictional irritation to the incised portion is limited to the time of insertion and extraction of the device in the course of operation, which can minimize the damage of the incised portion. Consequently the patient does not necessarily hospitalize for a long time, and moreover the patient can leave the hospital and return home on the day of the operation.

In the case of such blocking of nerve fiber, side effects may arise if nerve fiber other than aimed one should be unnecessarily blocked. Therefore the decision of which nerve fiber among a number of nerve fibers running in parallel should be blocked is important and sometimes it may decide success or failure of the operation. In the operation using the appliance of this invention, the endoscope inserted in the power supplying appliance is protruded beyond the power supplying appliance so that the power supplying appliance is outside the view field of the endoscope, the operator observes an incising portion in wide view field by a display, easily finding a bundle of nerve fiber, once the operator brings the target nerve fiber fascicle into view, moves gradually the endoscope into the power supplying appliance while keeping the nerve fiber fascicle in view. And focusing by controlling the position of the endoscope with fine adjustment so that both the nerve fiber fascicle and the electrode of the power supplying appliance are in view of the endoscope. After setting the endoscopes at said position, search for identifying nerve fibers to be blocked is performed. More specifically, as said above, approaching the electrode to specific nerve fibers and stimulating the nerve fibers by week power current while controlling the voltage by a voltage controller. While observing responses to the stimulation of respective parts of the body, repeating the electric stimulation to respective nerve fibers sequentially, target nerve fiber is stepwise identified. After identifying the nerve fiber, the power current is strengthened for nerve-fiber blocking to block the target nerve fiber. In this manner, using needle-shaped electrode, only target nerve fiber may be blocked by identifying the target nerve fiber by observing responses of respective parts of the body against electric stimulation by stimulating a specific nerve fiber in the nerve fiber fascicle with the weak power current. Typical cases where such nerve fiber blocking is effective are, for example, hyperhidrosis, Raynaud's syndrome and reflex sympathetic dystrophy syndrome (RSD).

It is preferred to make a slit at the end area, especially at the side of the end, of the power supplying appliance of this invention. The slit is a hole penetrating through inside to outside the cylinder unit of the power supplying appliance. There is no limitation in particular as to the shape of the slit and the shape may be a circle, a semicircle or polygons such as tetragon, however a circle or semicircle is preferred in view of easiness of processing or sterilization. The number of slit may be one or more than two. The slit enables the operator to observe continuously the view inside and outside the cylinder unit through the slit while electrification treatment is performed in the operation when the endoscope is drawn into the power supplying appliance, further the slit enable the operator to avoid losing view because of white smoke formed by electrification inside the cylinder unit during coagulation or cautery by ventilating white smoke in front of the endoscope optical lens through the slit. Although use of transparent plastics, glass or lens may be enough if only observing outside the cylinder unit, the important role of the slit is to ventilate the white smoke formed in the cylinder unit to outside the cylinder unit. In the case of needle-shaped electrode, the slit may be made near to the electrode. The operator thereby may observe an operation area through the opening of the inside wall of the cylinder unit and outside the cylinder unit through the slit.

BEST MODE FOR CARRYING OUT THE INVENTION

Figure 1:
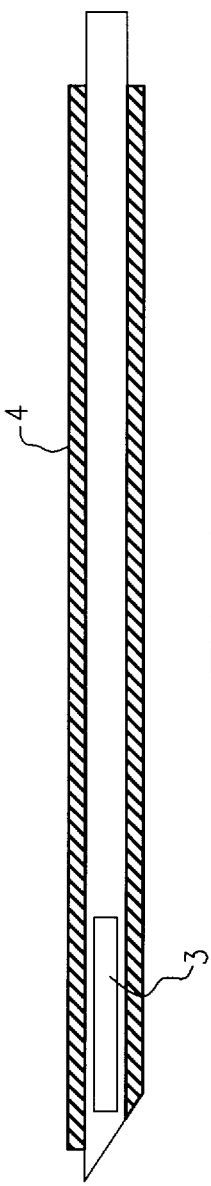
FIG. 1 is a front view of an endoscope power supplying appliance of the present invention.
Figure 2:
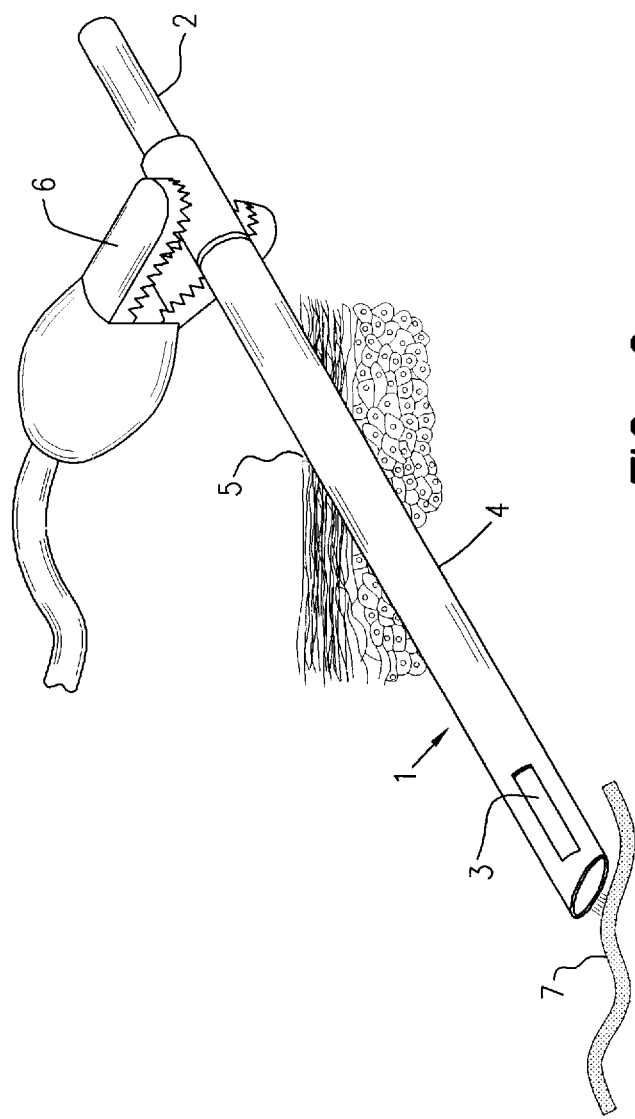
FIG. 2 is a conceptual diagram of use condition of the endoscope power supplying appliance during operation.
Figure 3:
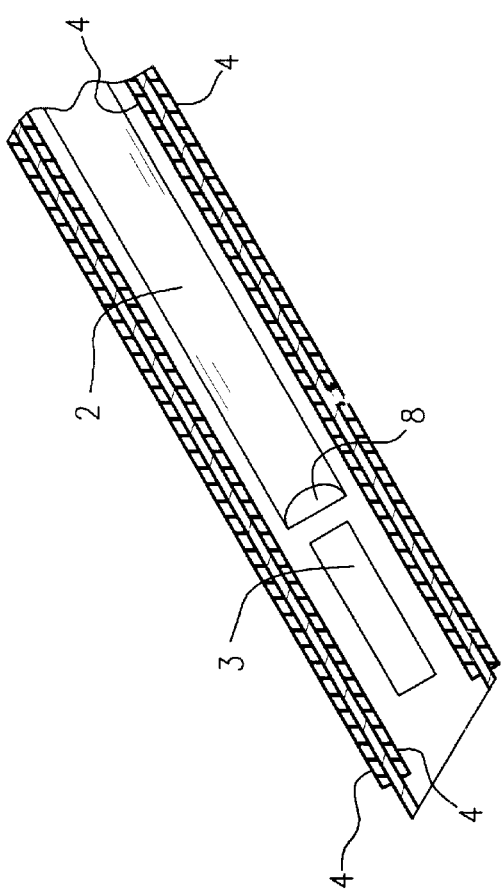
FIG. 3 is a sectional view of a distal end of the endoscope power supplying appliance.

FIGS. 1 to 3 illustrate an example of the endoscope power supplying appliance of the present invention. FIG. 1 is a front view viewing from the direction perpendicular to the axial one. This appliance adopted a monopolar electrode and an alligator clip is used for setting the second electrode on a body of a patient as shown in FIG. 2. This appliance is composed of an electrode, cylinder unit and control unit and they are integrally constructed by stainless steel. Electrical insulation treatment is processed as shown 4 in FIG. 1 except the electrode and an area the alligator grip is applied to. The electrode end is obliquely cut, the cut surface is not applied to the insulation treatment and forms an electrode. A rectangular slit 3 is opened at the cylinder unit approximately perpendicular to the position of the distal end of the electrode. The end of the electrification section by the alligator grip 6 in this appliance forms a control unit.

FIG. 2 is a conceptual diagram of use condition of the endoscope power supplying appliance during operation. Numeral 5 in the figure shows a skin incised portion, the incision may be performed using this appliance inserting the appliance in the body or another device inserting in said appliance. Numeral 2 is the endoscope, FIG. 2 shows the stage just before the operation of electric coagulation, the endoscope is drawn inside the cylinder unit and is in the position both the electrode and the operation site of electric coagulation are observable. Numeral 7 is a site electric coagulation is performed and the electrode approaches 7 before contact. At this stage, when performing other treatment such as laser treatment or ultrasonic treatment together with or instead of the electric coagulation, the operator may draw out the endoscope and insert a device corresponding to the operator's hope into the cylinder unit. In this case as it is not necessary to draw out the power supplying appliance itself out of the incised portion, no friction or irritation is caused and a number of treatments may be performed safely and surely.

FIG. 3 is a sectional view of the distal end of the present appliance. Numeral 8 shows an optical lens of the endoscope and circumferential observation from inside the cylinder unit through the slit 3 is possible for the endoscope 2

Figure 4:
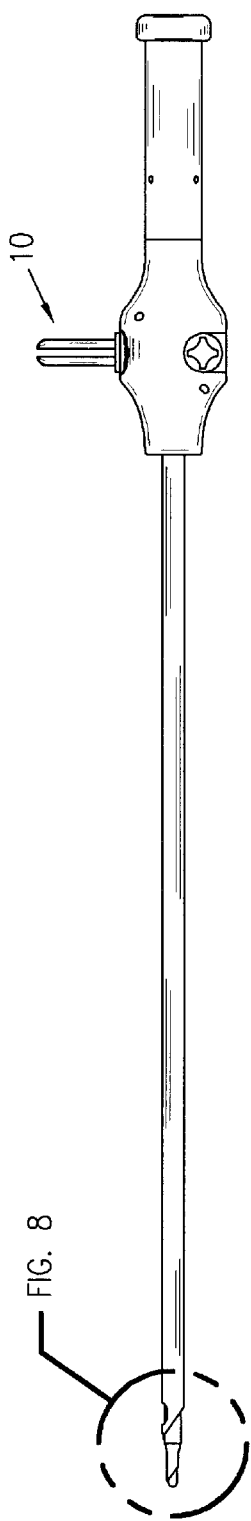
FIG. 4 is a front view of another example of an endoscope power supplying appliance of this invention.
Figure 7:
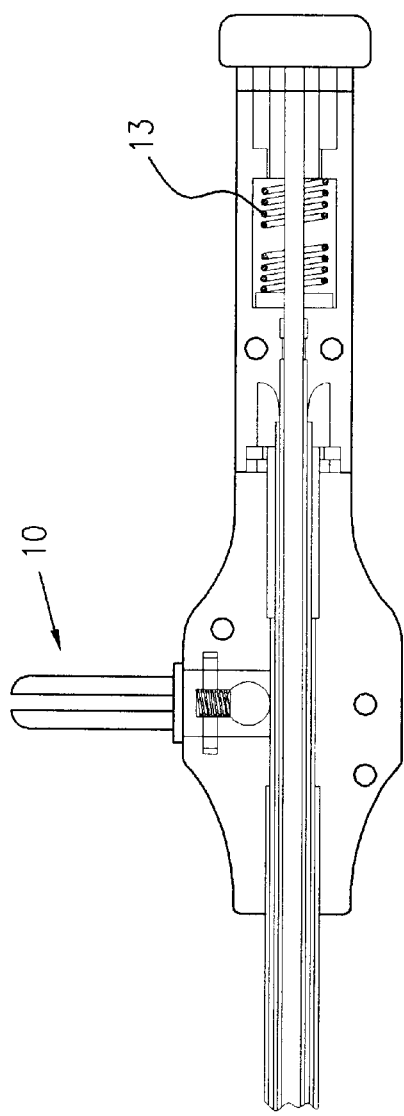
FIG. 7 is a B—B line sectional view of the control unit of FIG. 5.

FIG. 4 is a front view of another example of an endoscope power supplying appliance of this invention suitable in particular to blocking operation of thoracic sympathetic nerves under endoscope. The outer diameter of the cylinder unit up to control unit of this cylindrical electrode is 4.9 mm and the inner diameter is 4.5 mm, whole length of the appliance is about 20 cm, and the length of the control unit is 9.1 cm. An electrode terminal 10 protrudes from the operation unit, connects to a control unit (not shown in the drawing) via an electric code, and control unit controls voltage loaded on the electrode. FIG. 7 shows a sectional view of the operation unit. A spring 13 is set as a protective instrument so as not to injure tissue in the body or not to break endoscope when the endoscope contacts any tissue in the body during, the operation of the endoscope power supplying appliance of this invention in the body.

Figure 6:
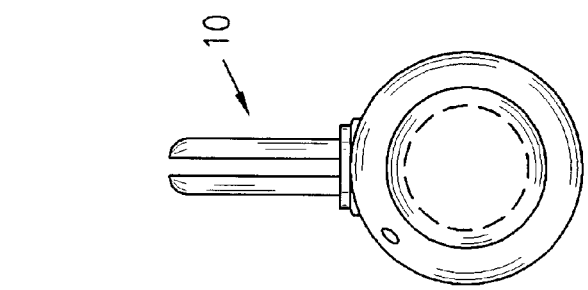
FIG. 6 is a right side view of the control unit.
Figure 5:
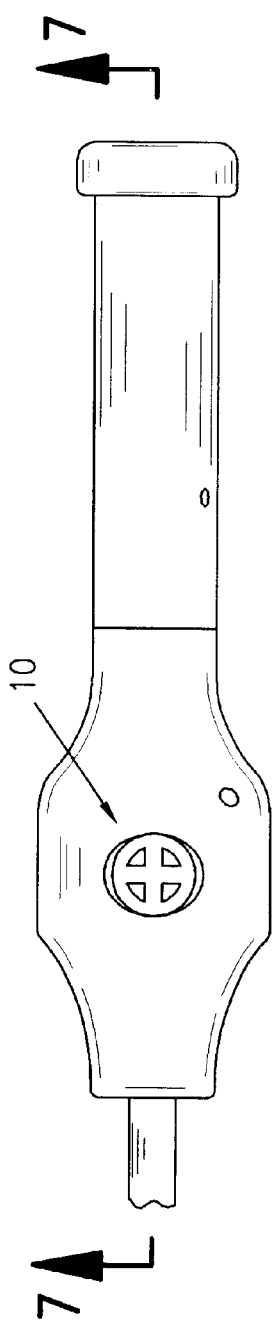
FIG. 5 is a plan view of a control unit of the endoscope power supplying appliance of FIG. 4.
Figure 8:
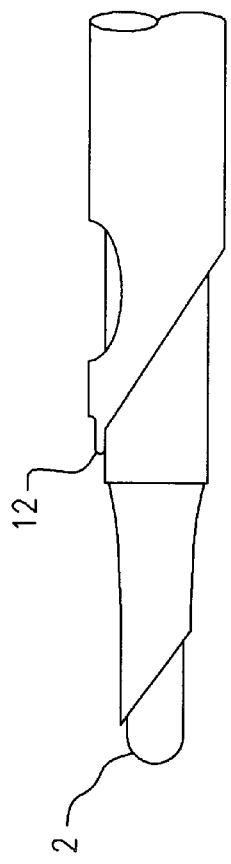
FIG. 8 is an enlarged view of an end section A of the endoscope power supplying appliance of FIG. 4.

FIG. 8 is an enlarged view of the distal end A of the endoscope power supplying appliance. The end of the electrode is obliquely cut, a needle-like end 12 is formed at the electrode tip end and a slit is opened near the side of the operation unit. The slit is semicircular in this Example. Numeral 2 is an endoscope, a lens part protrudes beyond the power supplying appliance, and the figure shows the state observing circumference including operation area with whole view field. Although only the end part is illustrated in this drawing, the length of the endoscope must be longer than the length between the electrode end and the operation unit end of the power supplying appliance and the length is 35 cm in this Example. The outer diameter of the cylinder unit is 4.45 mm which almost contacts the inner surface of the power supplying appliance and it is possible to move minutely and easily in the axial direction and to draw out of the appliance. FIG. 5 shows plan view of the operation unit and FIG. 6, right side view thereof.

INDUSTRIAL APPLICABILITY

The appliance is effective for operations such as fine vessel coagulation under endoscope, in particular, it is possible to perform thoracic sympathetic nerve blocking operation under endoscope with only one skin incision. As it is not necessary to draw out and insert the power supplying appliance through the incised portion, friction and irritation is caused only during inserting and drawing out through the incised, portion before and after the operation and injuries to the incised portion are minimized. Therefore long term hospitalization after operation is not necessary and patients can leave hospital and go home on the day of operation.

What is claimed is:

1. An endoscope power supplying appliance comprising an operation unit, a cylinder unit having a first distal end and a second end, and an electrode that is used by inserting an endoscope, wherein the electrode is set at the first distal end of the cylinder unit and the operation unit at the second end, an optical lens portion of the endoscope inserted into the power supplying appliance is capable of protruding beyond an end of the power supplying appliance, and the endoscope is operatively arranged to move along an axial direction of the power supplying appliance.

2. The endoscope power supplying appliance according to claim 1 which has a slit at a side of the distal end of the power supplying appliance.

3. The endoscope power supplying appliance according to claim 2 wherein the distal end of the power supplying appliance is in a blade shape.

4. The endoscope power supplying appliance according to claim 2 wherein the distal end of the electrode is in a needle shape.

5. The endoscope power supplying appliance according to claim 2 wherein a voltage loaded on the electrode is controllable.

6. The endoscope power supplying appliance according to claim 2 wherein back-and-forth movement of the endoscope in the power supplying appliance is controllable from the operation unit.

7. The endoscope power supplying appliance according to claim 2 wherein back-and-forth movement is performed using a linear muter.

8. The endoscope power supplying appliance according to claim 2 which is used for nerve blocking operation.

9. The endoscope power supplying appliance according to claim 2 where an operation may be performed by inserting a laser instrument except electric coagulation devices, ultrasonic endoscopes and ultrasonic operation devices instead of endoscopes.

10. The endoscope power supplying appliance according to claim 1 wherein the distal end of the power supplying appliance is in a blade shape.

11. The endoscope power supplying appliance according to claim 10 wherein the distal end of the electrode is in a needle shape.

12. The endoscope power supplying appliance according to claim 10 wherein a voltage loaded on the electrode is controllable.

13. The endoscope power supplying appliance according to claim 10 wherein back-and-forth movement of the endoscope in the power supplying appliance is controllable from the operation unit.

14. The endoscope power supplying appliance according to claim 10 wherein back-and-forth movement is performed using a linear muter.

15. The endoscope power supplying appliance according to claim 10 which is used for nerve blocking operation.

16. The endoscope power supplying appliance according to claim 10 where an operation may be performed by inserting a laser instrument except electric coagulation devices, ultrasonic endoscopes and ultrasonic operation devices instead of endoscopes.

17. The endoscope power supplying appliance according to claim 1 wherein the distal end of the electrode is in a needle shape.

18. The endoscope power supplying appliance according to claim 17 wherein a voltage loaded on the electrode is controllable.

19. The endoscope power supplying appliance according to claim 17 wherein back-and-forth movement of the endoscope in the power supplying appliance is controllable from the operation unit.

20. The endoscope power supplying appliance according to claim 17 wherein back-and-forth movement is performed using a linear muter.

21. The endoscope power supplying appliance according to claim 17 which is used for nerve blocking operation.

22. The endoscope power supplying appliance according to claim 17 where an operation may be performed by inserting a laser instrument except electric coagulation devices, ultrasonic endoscopes and ultrasonic operation devices instead of endoscopes.

23. The endoscope power supplying appliance according to claim 1 wherein a voltage loaded on the electrode is controllable.

24. The endoscope power supplying appliance according to claim 23 wherein back-and-forth movement of the endoscope in the power supplying appliance is controllable from the operation unit.

25. The endoscope power supplying appliance according to claim 23 wherein back-and-forth movement is performed using a linear muter.

26. The endoscope power supplying appliance according to claim 23 which is used for nerve blocking operation.

27. The endoscope power supplying appliance according to claim 23 where an operation may be performed by inserting a laser instrument except electric coagulation devices, ultrasonic endoscopes and ultrasonic operation devices instead of endoscopes.

28. The endoscope power supplying appliance according to claim 1 wherein back-and-forth movement of the endoscope in the power supplying appliance is controllable from the operation unit.

29. The endoscope power supplying appliance according to claim 28 wherein back-and-forth movement is performed using a linear muter.

30. The endoscope power supplying appliance according to claim 28 which is used for nerve blocking operation.

31. The endoscope power supplying appliance according to claim 28 where an operation may be performed by inserting a laser instrument except electric coagulation devices, ultrasonic endoscopes and ultrasonic operation devices instead of endoscopes.

32. The endoscope power supplying appliance according to claim 1 wherein back-and-forth movement is performed using a linear muter.

33. The endoscope power supplying appliance according to claim 32 where an operation may be performed by inserting a laser instrument except electric coagulation devices, ultrasonic endoscopes and ultrasonic operation devices instead of endoscopes.

34. The endoscope power supplying appliance according to claim 1 which is used for nerve blocking operation.

35. The endoscope power supplying appliance according to claim 34 wherein the nerve blocking operation is a blocking operation of sympathetic nerves in thoracic part under thoracoscope.

36. The endoscope power supplying appliance according to claim 35 where an operation may be performed by inserting a laser instrument except electric coagulation devices, ultrasonic endoscopes and ultrasonic operation devices instead of endoscopes.

37. The endoscope power supplying appliance according to claim 34 where an operation may be performed by inserting a laser instrument except electric coagulation devices, ultrasonic endoscopes and ultrasonic operation devices instead of endoscopes.

38. The endoscope power supplying appliance according to claim 1 where an operation may be performed by inserting a laser instrument except electric coagulation devices, ultrasonic endoscopes and ultrasonic operation devices instead of endoscopes.

* * * * *